United States Patent [19]

Commarieu et al.

[11] Patent Number: 6,020,530
[45] Date of Patent: Feb. 1, 2000

[54] PROCESS FOR PURIFICATION OF DIMETHYL SULPHOXIDE (DMSO)

[75] Inventors: Annie Commarieu, Courbevoie; Francis Humblot, Lanneplaa, both of France

[73] Assignee: Elf Atochem S.A., France

[ * ] Notice: This patent is subject to a terminal disclaimer.

[21] Appl. No.: 09/078,479

[22] Filed: May 14, 1998

[30] Foreign Application Priority Data

May 15, 1997 [FR] France .................................. 97 05965

[51] Int. Cl.⁷ .................................................. C07C 315/06
[52] U.S. Cl. ............................. 568/37; 210/660; 210/638
[58] Field of Search .............................. 568/37; 210/638, 210/660, 681, 687

[56] References Cited

FOREIGN PATENT DOCUMENTS 2014385   4/1970   France .

OTHER PUBLICATIONS

Alan M. Phipps, "Anion Exchange in Dimethyl Sulfoxide", *Analytical Chemistry* 40(*12*):1769–1773 (1968).

Chaudron et al., "La Purification du Dimethylsulfoxyde: criteres de purete", *Chimie Analytique* 53(5):310–314 (1971) (copy to be provided).

Copy of French Search Report dated Jan. 28, 1998.

*Primary Examiner*—Gary Geist
*Assistant Examiner*—Jean F Vollano
*Attorney, Agent, or Firm*—Bell, Boyd & Lloyd

[57] ABSTRACT

To purify a dimethyl sulfoxide (DMSO), this DMSO is placed in contact with an ion exchange resin of sulfonic type in —$SO_3NH_4$ form, and the DMSO is then separated from the resin. The DMSO thus obtained has an iron cation content lower than 1 ppb and a sodium cation content lower than 2 ppb.

5 Claims, No Drawings

PROCESS FOR PURIFICATION OF DIMETHYL SULPHOXIDE (DMSO)

FIELD OF THE INVENTION

The present invention relates to a process for the purification of dimethyl sulphoxide (DMSO) and to the DMSO thus purified.

BACKGROUND OF THE INVENTION

The DMSO currently available on the market is a product which is already of a good purity. Its commercial specifications are generally:

Purity: $\geq 99.7\%$ by chromatography

Acidity: $\leq 0.04$ mg KOH/g by potentiometry

Crystallization point: $\leq 18.1°$ C.

Visual appearance: $\leq$ clear

Water content: $\leq 0.15\%$

Colour (APHA): $\leq 10$

Patent FR 2 014 385 describes a process for the preparation of purified DMSO using an ion exchanger. In both examples of this patent a highly basic resin of the Amberlite IR-A 400 or Merck III type is employed to treat dimethyl sulphide/DMSO/10% sulphuric acid ternary mixtures. In fact, in this known process the purification seems to be essentially brought about by a fractional distillation of an aqueous solution of DMSO treated beforehand with an anion exchanger.

Analyses of trace metals have now been performed on a number of samples of commercial DMSO from various sources. These analyses are reported in Table 1.

The sodium, iron, potassium, calcium, chromium, copper, nickel and zinc concentrations have been measured by ICP (plasma torch-atomic emission spectrometry, Perkin Elmer instrument, Optima 3000 model) and are expressed in ppb (1 ppb=1 part by per thousand million=1 $\mu$g per kg).

The list of the metallic elements which appears in Table 1 is not exhaustive in respect of the metallic elements present in these samples.

TABLE 1

| Sample | Metal cations | | | | | | | |
|---|---|---|---|---|---|---|---|---|
| | Na | Fe | K | Ca | Cr | Cu | Ni | Zn |
| 1 | 40 | 13 | 60 | 20 | 2 | 10 | 8 | 10 |
| 2 | 39 | 60 | 3 | 13 | 13 | <2 | 18 | 3 |
| 3 | 30 | 40 | 3 | 20 | 12 | <2 | 15 | 3 |
| 4 | 30 | 40 | 3 | 14 | 13 | <2 | 15 | 3 |
| 5 | 30 | <1 | 20 | 25 | <2 | <2 | <3 | <3 |
| 6 | 70 | 90 | 65 | 55 | 15 | 2 | 25 | 60 |
| Detection limit | 2 | 1 | 3 | 2 | 2 | 2 | 3 | 3 |

For some applications, as for example in electronics or in pharmacy, the DMSOs analysed above contain too many metallic impurities. In general, a DMSO containing less than 10 ppb of each alkali and alkaline-earth metal and metal contaminant would be necessary for most of the uses in the abovementioned two technical fields.

DESCRIPTION OF THE INVENTION

The aim of the present invention is to find a process for purification of commercial DMSO which is already of a good purity, the latter being nevertheless insufficient for some applications.

Ion exchange by making use of resins is a technique widely employed for aqueous media and particularly allows deionized water to be obtained. Anion exchange in a liquid DMSO medium of low water content has already been carried out by Alan M. Phipps, Anal. Chem. 40(12) pp. 1769–1773, 1968, for the purpose of measuring the quantities of anions bound to the resin in experimental conditions approaching thermodynamic equilibrium.

It has now been found that the use of a resin in ammonium sulphonate form makes it possible, in DMSO of low water content or virtually anhydrous DMSO, to replace the metal cations $M^{n+}$ (n having values from 1 to 4) with ammonium anions (n $NH_4^+$).

The subject-matter of the invention is therefore a process for purification of dimethyl sulphoxide in order to decrease its content of alkali and alkaline-earth metal and metal cations, characterized in that it consists essentially in placing the DMSO to be purified in contact with a solid consisting of an ion exchange resin of sulphonic type which has its active groups in ammonium sulphonate form ($SO_3NH_4$) and in then separating from the solid the liquid consisting of the purified DMSO with very low contents of alkali and alkaline-earth metal and metal cations, by any appropriate known means, especially filtration, percolation or centrifuging.

A DMSO of low water content is advantageously treated, this content being preferably lower than or equal to 0.15% by weight relative to the total weight.

The sulphonic resin is preferably based on a polystyrene-divinylbenzene copolymer. In fact, these resins have a backbone which stands up to chemical attacks and, in particular, they do not dissolve in DMSO. These resins are generally defined by their divinylbenzene content. In fact, the latter determines the degree of crosslinking of the resin and hence the size of the pores in which the cation exchange takes place on the atomic scale.

The divinylbenzene in the copolymer preferably represents from 50 to 60% by weight and the polystyrene from 50 to 40% by weight relative to the total weight of the copolymer, without taking the $SO_3NH_4$ groups into account. This divinylbenzene content ensures a good kinetic activity of the exchange of the $M^{n+}$ cations with n $NH_4^+$.

The contact of the DMSO to be purified with the ion exchange resin is brought about at a temperature ranging from 18.45° C. (melting point of DMSO) to 120° C. (thermal stability limit temperature of the resins). This temperature is advantageously between 19 and 80° C., preferably between 20 and 50° C.

To define the quality of the DMSO capable of being obtained purified by the process according to the invention, iron and sodium have been retained as tracer elements and indicators of the general content of alkali and alkaline-earth metal and metal cations.

This purified DMSO is characterized in that it has an Fe cation content lower than or equal to 1 ppb and an Na cation content lower than or equal to 2 ppb, the respective limits of detection of the analysis method using plasma torch-atomic emission spectrometry.

EXAMPLES

The invention will be understood better with the aid of the following experimental part describing an example of embodiment of the present invention.

Experimental Part

I. Analysis Method

ICP (plasma torch-atomic emission spectrometry) was employed for analysing the traces of metals in the DMSO:

the sample is introduced into a plasma torch, the various elements present are excited and emit photons whose energy is characteristic of the element, since it is defined the electron structure of the element in question. A Perkin Elmer instrument (Optima 3000 DV model) was employed routinely.

II. Methodology

Principle: the metal traces are in $M^{n+}$ form. On passing the DMSO over a cation exchange resin, the latter itself in $NH_4^+$ form, the $M^{n+}$ ions in solutions are replaced with n $NH_4^+$.

III. Test

Principle: with the aim of simplifying the analyses, sodium and iron were chosen as tracers representing all of the metallic impurities present in the DMSO.

Sodium is characteristic of the atmospheric and accidental contamination (dust, environment) and iron is characteristic of the contamination that can originate from the process (unit made of stainless steel).

DMSO doped with 1000 ppb of iron and 1000 ppb of sodium was placed in contact with a cation exchange resin in $NH_4^+$ form (2 g of resin per 100 g of DMSO) at 25° C. Samples of DMSO were taken in the course of time. The changes in the iron and sodium concentrations could thus be followed with time.

The resin employed was of the sulphonic type, supplied by the Purolite company under reference MN 500. It is characterized especially by a divinylbenzene/styrene ratio of between 50/50 and 60/40. It was pretreated to obtain the $H^+$ form in the following manner: through 90 ml of resin placed in a column, 540 ml of 5% HCl are passed at a flow rate which is constant and such that the operation takes 30 to 45 minutes. The resin was then rinsed with deionized water until the water coming out was neutral. The resin thus obtained in $H^+$ form was next treated to obtain the $NH_4^+$ form in the following manner: over the 90 ml of resin placed in the column, 500 ml of an aqueous ammonia ($NH_4OH$) solution at a concentration of 2.5% are passed at a flow rate which is constant and such that the operation takes 30 to 45 minutes. After having been rinsed with demineralized water until the water coming out was neutral, the resin was dried by suspension in methanol and evaporation under vacuum in the rotary evaporator (90° C., 2000 Pa) until a constant weight was observed.

Table 2 shows the change in the iron and sodium concentration in the DMSO as a function of time.

TABLE 2

| Time (min) | 0 | 5 | 10 | 20 | 45 | 60 | 90 | 120 |
|---|---|---|---|---|---|---|---|---|
| [Na] (ppb) | 980 | 120 | 50 | 21 | 10 | 6 | <2 | <2 |
| [Fe] (ppb) | 1020 | 350 | 150 | 70 | 25 | 15 | 6 | <1 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for purification of dimethyl sulphoxide (DMSO) to decrease its content of alkali and alkaline-earth metal and metal cations, comprising placing the DMSO to be purified in contact with a solid consisting of an ion exchange resin of sulphonic type which has its active groups in ammonium sulphonate form ($SO_3NH_4$) and in then separating from the solid the liquid consisting of the purified DMSO with very low contents of alkali and alkaline-earth metal and other metal cations.

2. Process according to claim 1, wherein a DMSO of low water content is treated, this content being lower than or equal to 0.15% by weight relative to the total weight.

3. Process according to claim 1, wherein the resin is based on a polystyrene-divinylbenzene copolymer.

4. Process according to claim 1, comprising the contact of the DMSO to be purified with the ion exchange resin is brought about at a temperature of 19 to 80° C.

5. Process according to claim 4, wherein the temperature is between 20 and 50° C.

* * * * *

UNITED STATES PATENT AND TRADEMARK OFFICE
CERTIFICATE OF CORRECTION

PATENT NO.   : 6,020,530
DATED        : February 1, 2000
INVENTOR(S)  : Commarieu et al.

It is certified that error appears in the above-identified patent and that said Letters Patent is hereby corrected as shown below:

<u>Title page,</u>
Item [73], Assignee, should read -- Elf Aquitane Exploration Production France --.

Signed and Sealed this

Fifteenth Day of October, 2002

*Attest:*

*Attesting Officer*

JAMES E. ROGAN
*Director of the United States Patent and Trademark Office*